United States Patent [19]

Albarella et al.

[11] Patent Number: 5,424,215
[45] Date of Patent: Jun. 13, 1995

[54] ASSAY FOR THE DETERMINATION OF PROTEIN IN A BIOLOGICAL SAMPLE

[75] Inventors: James P. Albarella, Granger; Angela A. Michaels, Elkhart; Michael J. Pugia, Granger; Ronald G. Sommer, Elkhart, all of Ind.

[73] Assignee: Miles Inc., Elkhart, Ind.

[21] Appl. No.: 192,345

[22] Filed: Feb. 7, 1994

[51] Int. Cl.⁶ .................................. G01N 33/00
[52] U.S. Cl. .................................. 436/86; 436/87; 436/88; 436/169; 422/56; 422/57; 422/58
[58] Field of Search ............... 422/56, 57, 58; 436/86, 436/87, 88, 169

[56] References Cited

U.S. PATENT DOCUMENTS

| | | | |
|---|---|---|---|
| 4,013,416 | 3/1977 | Rittersdorf et al. | 422/56 |
| 4,870,005 | 9/1989 | Akiyoshi et al. | 435/7 |
| 5,279,790 | 1/1994 | Corey et al. | 422/56 |

*Primary Examiner*—Robert J. Warden
*Assistant Examiner*—N. Bhat
*Attorney, Agent, or Firm*—Roger N. Coe

[57] ABSTRACT

The detection of protein is accomplished using novel composition and method involving phenolsulfonephthalein protein error indicator, buffer and an aliphatic ether-polycarbonate present in an amount equal to or less than ten percent by weight.

4 Claims, No Drawings

ASSAY FOR THE DETERMINATION OF PROTEIN IN A BIOLOGICAL SAMPLE

BACKGROUND OF THE INVENTION

1. Field Of The Invention

The present invention relates generally to the detection of protein and, more particularly, to a novel composition and method for the determination of protein in a biological sample utilizing phenolsulfonephthalein protein error indicator, buffer and an aliphatic polyether-polycarbonate present in an amount equal to or less than ten percent by weight.

2. Description Of The Background Art

The determination of the presence of protein in a biological sample is of the utmost importance in the diagnosis of several pathological conditions affecting the kidney, circulatory system and central nervous system. Accordingly, it is frequently necessary to quantitatively and/or qualitatively measure protein (albumin) in urine. This is especially important in the diagnosis of diabetes and kidney disease. The predominant protein in diabetes determinations is albumin; hence the model system for protein urine testing is albumin.

Methods for determining the presence of albumin in urine are well known. The most inexpensive and convenient method for albumin determination involves wetting a paper test strip impregnated with a protein error indicator with a small quantity of urine. If albumin is present in the urine sample, the test strip will indicate this by simply changing color. The color observed normally varies depending on the concentration of albumin in the sample. This variable color change is used to quantify the albumin in the sample.

While test strips of the above type are convenient and rapid vehicles for on-the-spot determinations of protein, one of the problems which has occurred is the so-called specific gravity effect. Typically tests for urinary protein use a pH indicator dye which shows a shift in pKa when complexed with protein (the "protein error" of pH indicators). This method does not provide sufficient separation between negative urine and those containing trace concentrations of protein (approximately 15 micrograms per deciliter) and gives false positive readings in urine of high specific gravity. It has been found that the addition of certain polycarbonate compounds to the protein error indicator both lowers the initial reactivity of the reagent paper and decreases the tendency for high specificity gravity urine samples to give a positive reading for protein.

Another problem which has occurred with the construction of such devices is that the absorbent material, usually filter paper, does not have consistent (i.e., uniform) reactivity with the reagents used in the system. Filter paper lots often interact with the reagents required for the determination of protein to a greater extent than the same carrier matrix material reacts with reagent compositions for the determination of other analytes.

The problems of adjusting the formulations to obtain uniform reactivity between the reagent composition and the carrier matrix material employed has been a long-standing problem in the field and one of significant importance to the industry. Initially it was believed that adjustment of the pH of the reagent composition would overcome the problem of the variability in the reactivity of the reagent composition and the carrier matrix material. pH adjustments, however, were not effective for all lots of carrier matrix material. The desired result was to achieve a reagent composition which would result in a lighter negative color and a darker positive color. Triton X-100, a polyethylene surfactant, was found to have an impact on reactivity but produced a lighter color at both the negative and positive ends of the color range.

Other means of adjusting reactivity were investigated. For example, all components of the reagent composition were varied but these variations were not found effective in producing the desired lighter negative color and a darker positive color. Polyvinyl alcohol also was introduced into the reagent composition and found to be ineffective in controlling reagent reactivity characteristics with differing lots of carrier matrix.

Thus, even with appropriate quality control and by trying to implement effective screening and invention/restrictions reactivity problems between differing lots of carrier matrix material could not be controlled effectively.

To overcome the reactivity problem mentioned above for the determination of protein an unique reagent composition was prepared and formulated in such a way that the variability in reactivity between the reagent composition and the carrier matrix has been substantially eliminated. Moreover, the reduction of urine pH variability on assay results is another observed benefit of the reagent composition.

SUMMARY OF THE INVENTION

The present invention provides an analytical test strip for the detection of protein in a biological sample comprising an absorbent carrier matrix impregnated with a phenolsulfonephthalein protein error indicator, a buffer and aliphatic polyether-polycarbonate present in an amount equal to or less than 10% by weight.

In accordance with the invention, a two-dip impregnation procedure of the absorbent carrier with the reagent composition is used in which buffer and optionally a background dye such as FD&C Yellow #5 and FD&C #3 are first impregnated into the absorbent carrier from an aqueous solution and the polyhalogenated phenolsulfonephthalein protein error indicator and aliphatic polyether-polycarbonate compounds are impregnated in a second dip using a nonaqueous solvent such as an alcohol solution.

Another aspect of the present invention is directed to a method for the detection of protein in a biological sample in which an analytical test strip is wetted with the biological sample. The wetted test strip comprises an absorbent carrier impregnated with the reagent composition described above. The test strip is observed to detect any color change which is indicative of both the presence and the amount of protein in the biological sample.

DESCRIPTION OF THE PREFERRED EMBODIMENTS

In accordance with the invention, it has been discovered that test strips for the determination of protein in biological fluids can be prepared without any significant reactivity problems between carrier matrix and the reagent composition for varying lots of the carrier matrix. In addition, it has been found that the influence of urine variability on detection limits, both for visual detection and instrumental detection is reduced by the reagent composition of the present invention.

The present invention is achieved by impregnating an absorbent carrier matrix with the reagent composition. The absorbent carrier matrix is preferably filter paper. A preferred filter paper is grade 204 obtained from Ahlstrom Filtration Inc. which contains a mixture of wood and cellulose pulps. This filter paper differs from lot to lot. Screening and inventory restrictions have in the past been ineffective in guaranteeing optimal reagent performance.

Other materials useful as an absorbent carrier include felt, porous ceramic strips and woven matted glass fibers (described in U.S. Pat. No. 3,846,247). Also suggested as suitable absorbent carriers of test strips are materials such as wood, cloth, sponge materials and argillaceous substances (as described in U.S. Pat. No. 3,552,928). It has been found, however, that filter paper is especially suitable despite the variations which exist from lot to lot.

The absorbent carrier matrix is impregnated with a reagent composition in the manner indicated above. It has been found that a two-dip impregnation procedure using an aqueous first dip and a nonaqueous solvent solution second dip provides optimum results. The absorbent strip preferably contains a buffer to adjust the pH to between about 1.5 and 4.5. Preferably, the system is adjusted to a pH of about 3.5 and most preferably about 3.7. The nature of the buffer system, however, is not critical. Any well known buffering material can be employed. Preferred buffers is include citric acid and sodium citrate.

If the buffer is greater than 9.3 g/dl. (grams per deciliter) reagent runover can be a problem and if the buffer is less than 7.1 g/dl. the buffering may not be sufficient. An amount of buffer equivalent to about 8.7 g/dl. is optimal.

In addition to the buffering material, red dye and yellow dye are optionally added during the first dip. Any red dye suitable for reagent compositions can be used. However, FD&C red dye #3 is a preferred material. A preferred yellow dye is FD&C yellow #5. The dyes mask urine coloration at negative color levels. Other dyes, surfactants and the like can also be added to the first dip as additional optional components.

Generally, dye in excess of about 40 g/100 liters and less than 60 g/100 liters can be used. For tetrabromophenol blue (TBPB), 50 g/100 liters is optimal.

In the second dip a nonaqueous solvent, preferably ethanol, solution is used in order to reduce evaporation. Conventional polyhalogenated phenolsulfonephthalein protein error indicators can be employed as the indicator compound. Suitable materials include:

3,4,5,6-Tetrabromophenolsulfonephthalein (TBPSP);
3',3"-Dibromo-3,4,5,6-tetrabromophenolsulfonephthalein (DBTB);
3',3"-Diiodo-3,4,5,6-tetrabromophenolsulfonephthalein (DITB);
3',3",5',5"-Tetrachloro-3,4,5,6-tetrabromophenolsulfonephthalein (TCTB);
3',3",5',5"-Tetrabromo-3,4,5,6-tetraiodophenolsulfonephthalein (TBTI);
3",3",5',5"-Tetraiodophenol-3,4,5,6,-tetrabromosulfonephthalein (TITB);
3',3"-Disulfo-5',5"-dicholoro-3,4,5,6-tetrabromophenolsulfonephthalein (DSDC);
3',3"-Disulfo-5',5"-dibromophenol-3,4,5,6-tetrabromosulfonephthalein (DSHB).

Tetrabromophenolsulfonephthalein is a preferred material.

The other essential ingredient of the second dip reagent composition is an aliphatic polyether-polycarbonate material. The preferred materials are prepared using diphenylcarbonate and a difunctional hydroxy (alcohol) compound or mixtures of difunctional hydroxy compounds. The identification of the polycarbonates, their molecular weights and the alcohols used in their preparation are listed in the following table:

TABLE 1

| Identification No. | Alcohol Compound | Ratio | Molecular Weight |
|---|---|---|---|
| KOK 9209 | tetraethylene glycol/ hexanediol-1,6 | 1 | 1795 |
| KOK 10,000 | tetraethylene glycol/ hexanediol-1,6 | 1 1 | 4187 |
| KOK 10,001 | triethylene glycol | — | 1972 |
| KOK 10,002 | triethylene glycol/ tetraethylene glycol | 1 | 1972 |
| KOK 10,071 | polyether L-950 (polypropylene glycol MW about 420 g/mole) | — | 1594 |

The last material in Table 1 is particularly preferred. This polypropylene oxide carbonate copolymer, prepared by the Titanium (IV) butoxide catalyzed condensation of Polyether L 950 ® material (Bayer AG) with diphenyl carbonate has the structure

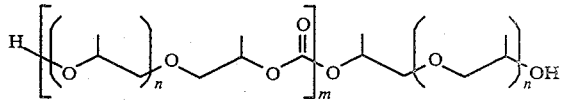

The starting material Polyether L 950 is a difunctional polypropylene glycol with a number average molecular weight of about 420, prepared by polymerizing propylene oxide in the presence of 1,2-propanediol. A polymer chain grows off of each of the diol residues, resulting in a linear polyether with each end terminating in a secondary hydroxyl group (i.e., a hydroxyl group functionality of two). The polyether-polycarbonate material results from the connection of polyether residues with carbonate linkages in the following proportions:

|  | amt (g) | amt (mol) |
|---|---|---|
| Polyether L 950 | 4248 | 10.22 |
| Diphenyl Carbonate | 1581 | 7.39 |
| Ti(OC$_4$H$_9$)$_4$ | 0.6 | 0.0018 |

It has been found important to limit the amount of aliphatic polyether-polycarbonate material to 10% by weight or less for reducing the specific gravity effect. With respect to reducing filter paper effects it is then found desirable to limit the amount of aliphatic polyether polycarbonate material to two percent by weight or less.

The following examples are presented to describe preferred embodiments and utility of the present invention and are not meant to limit the present invention unless otherwise stated in the claims appended hereto.

EXAMPLE 1

A. Preparation of protein reagent paper containing polycarbonates and of control reagents without polymer These unbuffered protein reagents were used with buffered test solutions for purposes of identifying useful polymers.

Dip solution: 0.3 mM tetrabomophenol blue, TBPB, and 0.1% or 1.0% (w/v) polycarbonate in THF. (Control reagents were prepared with identical dip solutions which did not contain a polymer.)

The dips were impregnated into Whatman CCP-500 paper using a web speed of 4 ft/min and drying temperatures of 60° C. The reagent paper was processed into reagent strips containing 0.2×0.2 inch pads.

B. Measurement of the Reactivity of the Reagents
  1. Samples. The reagents were dipped into 0.20M potassium citrate buffer either pH 3.5 or 4.0, and either containing or not containing 20 mg/dL Human Serum Albumin (HSA).
  2. Instrumental Readings. The percent reflectance at 630 nanometers (nm) (610 nm can also be used) was measured 20 seconds (s) after dipping the strip in the sample on a CLINITEK® 200 instrument. The K/S was calculated according to the equation $K/S=(1-R)^2/2R$. Each value is the mean of ten replicate measurements.

C. Results and Discussion
  1. Data.

TABLE 2

| | pH 3.5 Results | | | | |
| | K/S at 630 nm at 20 s (standard deviation) | | | | |
| Polymer | No HSA | 20 mg/dL HSA | Slope | % Reduction of Blank (1) | % Reduction of Slope (2) |
| --- | --- | --- | --- | --- | --- |
| None | 0.088 (.005) | 0.375 (.020) | 0.0144 | — | — |
| KOK 9209 (0.1% w/v) | 0.068 (.007) | 0.271 (.008) | 0.0102 | 56 | 29 |
| KOK 10,000 (0.1% w/v) | 0.079 (.002) | 0.283 (.008) | 0.0102 | 25 | 29 |
| KOK 10,000 (1.0% w/v) | 0.069 (.002) | 0.229 (.007) | 0.0080 | 53 | 44 |
| KOK 10,001 (0.1% w/v) | 0.077 (.003) | 0.322 (.018) | 0.0123 | 31 | 15 |
| KOK 10,002 (0.1% w/v) | 0.071 (.006) | 0.327 (.008) | 0.0128 | 47 | 11 |

(1) The K/S of blank paper has been found to be approximately 0.052; therefore % Reduction in blank - [{(K/S of blank:no polymer-0.052) - (K/s of blank:with polymer-0.052)} / (K/S of blank:no polymer-0.052)] × 100

(2) % Reduction in Slope = [(Slope:no polymer-Slope with polymer) / (Slope:no polymer)] × 100

Similar results were obtained at pH 4.0.

2. Discussion. In buffer solution at both pH 3.5 and 4.0, some polycarbonates reduce the blank more than they reduce the slope. It was postulated from this experiment that the addition of polycarbonates to complete protein reagent (containing both a buffer and TBPB) would lower the initial color (blank) and possibly reduce the incidence of false positive.

EXAMPLE 2

A. TBPB-10% KOK 10,071 Protein Reagent Formulation
  1. Buffer Stock Solution. Dissolve 14.75 grams (g) citric acid, 10.93 g sodium citrate, and 7.2 mg of FD&C Yellow #5 in 154 mL distilled water; pH=3.46.
  2. First Dip. (a) 17.94 g buffer stock solution; (b) 5.0 g ethanol and (c) 2.47 g distilled water.
  3. Second Dip. (a) 7.5 mg TPBP; (b) 2.5 g KOK 10,071 and (c) q.s. to 25 mL with THF.

B. The control formulation was prepared with the same first dip and with a second dip that it contained no polymer.

The dips were impregnated into E & D 237C paper using a web speed of 4 feet per minute (ft/min) and drying temperatures of 80° C. for the first dip and 60° C. for the second dip.

C. Measurement of the Reactivity of the Reagents.
  1. Samples. The samples used for testing were (1) a negative medium SG urine pool and HSA spiked into the medium SG urine pool to obtain a concentration of 15 mg/dL and (2) three clinically negative[1] high SG urine samples (SG=A, 1.028; B, 1.027;

[1] Clinically negative is defined as negative by the Sulfosal test and containing HSA≦2 mg/dL and total protein<10 mg/dL. The objective is to obtain a response for clinically negative urine that is a small portion of the response given by 15 mg/dL HSA.

and C, 1.027). the reactivities of these samples were measured on a CLINITEK® 200 instrument (three replicates per sample).

2. The data is shown below as the K/S for each of the samples. In addition the contribution by each of the high SG urine samples is shown as $[(K/S_{high\ SG}-K/S_{blank})/(K/S_{15\ mg/dL}-K/S_{blank})] \times 100$. This contribution is the percent of the 15 mg/dL HSA reactivity caused by the high SG urine.

TABLE 3

| | Effect of 10% KOK 10,071 on the Performance of the Protein Reagent | | | | | | | |
| | K/S at 630 nm (standard deviation) | | | | | | | |
| | Medium SG Urine | | High SG Urine | | | High SG Urine Contribution | | |
| Reagent | No HSA | 15 mg/dL HSA | A | B | C | A | B | C |
| --- | --- | --- | --- | --- | --- | --- | --- | --- |
| No Polymer | 0.165 (.016) | 0.29 (.013) | 0.258 (.012) | 0.238 (.017) | 0.240 (.019) | 74 | 58 | 60 |
| 10% KOK 10,071 | 0.073 (.005) | 0.137 (.002) | 0.088 (.013) | 0.092 (.004) | 0.086 (.011) | 23 | 30 | 20 |

Both the initial color and the reactivity to HSA are reduced by the 10% KOK 10,071. However, the contributions by the negative high SG urine are also reduced considerably. Therefore, the presence of the 10% KOK 10,071 polymer appears to reduce the possibility for the high SG urine samples to give false positive results.

Another example compared TBPB containing protein reagent with and without 4% KOK 10,071.

EXAMPLE 3

A. TBPB-KOK Protein Reagent Formulation (amounts to prepare 100 mL dips)
1. First Dip (0.45M sodium Citrate-pH 3.70, 0.03 mM FD&C Yellow; aqueous solution). (a) 50 mL 0.9M sodium citrate, pH-3.70; (b) 3.0 mL 1 mM FD&C yellow #5; and (c) 47 mL distilled water.
2. Second Dip (0.30 mM TBPB, 4% (w/v) KOK 10,071; in THF). (a) 30 mL 1 mM TBPB in THF; (b) 40 mL 10% KOK 10,071 in THF; and (c) 30 mL THF.

The control formulation was prepared with the same first dip and with a second dip that contained no polymer. The dips were impregnated into E&D 237C paper as in Example II.

B. Measurement of the Reactivity of the Reagents.
1. Samples. The samples in the medium SG urine were spiked with HSA as stated above. One clinically negative high SG urine (A; SG=1.030; pH=5.6) and one contrived alkaline high SG urine pool (B; SG=1.024; pH=8.7) were used to test for possible false positive readings. High SG urine "B" was used as a "worst case" example to test the limits of the KOK polymer effect. Six replicate measurements of each sample were made on CLINITEK® 200+ instruments and the data is shown below:

TABLE 4

Effect of 4% KOK 10,071 on the Performance of the Protein Reagent

K/S at 630 nm
(standard error with 90% confidence

| Reagent | Medium SG Urine No HSA | 15 mg/dL HSA | High SG Urine A | High SG Urine B | High SG Urine Contribution A | High SG Urine Contribution B |
|---|---|---|---|---|---|---|
| No Polymer | 0.268 (.012) | 0.458 (.023) | 0.379 (.011) | 0.430 (.023) | 58 | 85 |
| 4% KOK 10,071 | 0.110 (.002) | 0.241 (.007) | 0.145 (.004) | 0.177 (.004) | 26 | 51 |

As in the second example, the initial color and the reactivity to HSA are reduced by the polycarbonate KOK 10,071. Also similarly, the contributions of the negative high SG samples are reduced with respect to the reagent with no polycarbonate. This confirms that the polycarbonate reduces the possibility for the high SG urine samples to give false positive results.

EXAMPLE 4

An aqueous solution (10 liters), adjusted to a final pH of 3.7, having 417 g. sodium citrate, 455 g. citric acid, 0.29 g. of FD&C yellow #5 and 0.5 g. of FD&C red #3 and 24 g. of PVA was used to impregnate filter paper grade 204C.

After the first dip had dried (at temperatures of 80°-100° C.) the filter paper was impregnated with a second solution. The second solution (10 liters) was an ethanol solution of 5 g. of tetrabromophenolsulfonephthalein, 50 g. of citric acid and 150 g. propylene oxide carbonate copolymer prepared by the titanium IV butoxide catalyzed condensation of polyether L 950 ® (Bayer AG) with diphenyl carbonate. The resulting material was then dried at temperatures from 35° to 105° C.

EXAMPLE 5

Paper lots which differ only in pulp lots cause large reactivity differences when used with protein reagent without KOK (Table 5). Differences in binding of dye and protein to the paper's fiber have been proposed as the cause of between lot differences. Furthermore, it has been proposed that increased binding of dye by paper would increase the background of the assay and that increased binding of protein by paper would decrease the protein response of the assay. Table 5 is based on using a central formula similar to that of Example 4 without KOK.

TABLE 5

| Grade | Lot | CLINITEK-10 Neg. Mean | CLINITEK-10 Pos. Mean | CLINITEK-200 Neg. Mean | CLINITEK-200 Pos. Mean | |
|---|---|---|---|---|---|---|
| 237 | 7775 | 672 | 525 | 695 | 479 | least background |
| 237 | 8079 | 745 | 549 | 824 | 511 | |
| 237 | 8137 | 753 | 560 | 839 | 529 | |
| 237 | 14014 | 706 | 551 | 743 | 510 | |
| 237 | 8977 | 743 | 586 | 800 | 572 | |
| 237 | 9241 | 740 | 595 | 787 | 555 | |
| 237 | 9041 | — | — | 761 | 570 | |
| 204 | 331 | 749 | 555 | 838 | 525 | |
| 204 | 225 | 772 | 578 | 866 | 545 | most background |
| 204 | 342 | 760 | 562 | 850 | 523 | |
| 204 | 14011 | 755 | 575 | 818 | 548 | |
| 204 | 14013 | 759 | 584 | 823 | 555 | |
| 204 | 306 | 740 | 563 | 805 | 537 | |
| 204 | 238 | 767 | 595 | 841 | 564 | |
| 204 | 9115 | — | — | 839 | 572 | |

Reagent reactivity is expressed as decode numbers for two separate Miles' instruments, the CLINITEK-10 and CLINITEK-200. Decodes numbers are based on % reflectance at the dyes absorbance maximum of 610 to 660 nm. Lower decode numbers indicate greater reactivity and more background color. The reagent pH is 3.46 for these determinations. The 237 and 204 filter paper grades are products of Alhstrom Filtration of Mt. Holly Springs, Pennsylvania.

The analytical test strip prepared in accordance with Example 4 was wetted with urine and the resulting color change was observed and recorded as an indication of protein in the urine biological sample.

A large reduction in the effect of filter paper lot has been achieved with the Protein 4 reagent "Pro 4" (based on Example 4) as seen in Table 6. This reduction increased manufacturability and made the reagent result more consistent. The polymer is thought to reduce the paper variation by disrupting the binding of the dye to the cellulose fibers. As a result, protein reagent reactivity can be held consistently at a target.

TABLE 6

| Formula | Reactivity Negative | 30 mg/dL |
|---|---|---|
| Pro 4 | 883 | 570 |
| | 863 | 570 |
| | 904 | 586 |

It was observed that even when different lots of filter paper were employed the reactivity between the reagent composition and filter paper was not a factor in the determination of protein. Moreover, the test strips showed a reduction of variability with respect to different urine samples for both visual and instrumental detection limits. This is contrary to other formulations utilized for the determination of protein in which detection limits for medium and high specific gravity urine often vary for both visual and instrumental readings.

While the invention is susceptible to various modifications and alternate forms, specific embodiments thereof have been shown by way of example and have been described in detail. It should be understood, however, that the examples are not intended to limit the invention to particular forms disclosed but on the contrary, the intention is to cover all modifications, equivalents and alternatives falling within the spirit and scope of the invention as defined by the appended claims.

What is claimed is:

1. A method for the detection of protein in a biological sample, which method comprises the steps of:
   (a) wetting an analytical test strip with a biological sample, the test strip including an absorbent carrier impregnated in a first aqueous dip with buffer added to adjust the pH to between 1.5 and 4.5 and then impregnating said absorbent carrier with a nonaqueous solvent solution consisting essentially of a potyhalogenated phenolsulfonephthalein protein error indicator and 10% or less by weight of an aliphatic polyetherpolycarbonate, and;
   (b) observing and recording any color change of the test strip, wherein a color change is indicative of protein in said biological sample.

2. The method of claim 1 in which the aliphatic polyether polycarbonate is present in 2% or less by weight and has the structure:

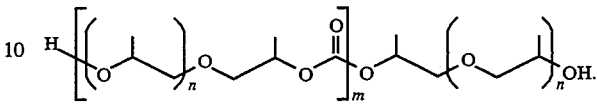

3. A test device for the determination of protein in a biological sample consisting essentially of a carrier matrix impregnated with a polyhalogenated phenolsulfonephthalein protein error indicator, a buffer to adjust the pH to between 1.5 and 4.5 and 10% or less by weight of an aliphatic polyether-polycarbonate.

4. The test device of claim 1 in which the aliphatic polyetherpolycarbonate is present in 2% or less by weight and has the structure:

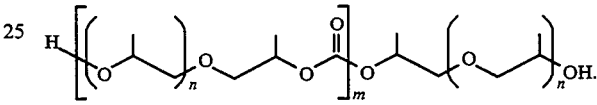

* * * * *